US007330263B2

(12) United States Patent
Ohtsuka

(10) Patent No.: US 7,330,263 B2
(45) Date of Patent: Feb. 12, 2008

(54) MEASUREMENT METHOD AND APPARATUS

(75) Inventor: Hisashi Ohtsuka, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 435 days.

(21) Appl. No.: 11/049,893

(22) Filed: Feb. 4, 2005

(65) Prior Publication Data

US 2005/0168746 A1   Aug. 4, 2005

(30) Foreign Application Priority Data

Feb. 4, 2004   (JP)   ............................. 2004-027458

(51) Int. Cl.
*G01N 21/55* (2006.01)
(52) U.S. Cl. ...................................... 356/445; 356/246
(58) Field of Classification Search ........ 356/445–448, 356/224, 246, 128, 136; 250/216, 227.14, 250/227.25, 458.1, 459.1, 461.1–461.2
See application file for complete search history.

(56) References Cited

U.S. PATENT DOCUMENTS

| | | | |
|---|---|---|---|
| 6,577,396 B1 | 6/2003 | Naya | |
| 6,697,158 B2 * | 2/2004 | Ogura et al. | 356/445 |
| 7,075,657 B2 * | 7/2006 | Sato | 356/455 |

2003/0075697 A1   4/2003   Ohtsuka et al.

FOREIGN PATENT DOCUMENTS

JP            6-167443 A      6/1994

OTHER PUBLICATIONS

Takayuki Okamoto, "Spectrum Researchers", Journal of The Spectroscopical Society of Japan, vol. 47, No. 1, 19998, pp. 21-23 and 26-27.

* cited by examiner

*Primary Examiner*—Gregory J. Toatley, Jr.
*Assistant Examiner*—Tri Ton
(74) *Attorney, Agent, or Firm*—Sughrue Mion, PLLC

(57) ABSTRACT

A measurement apparatus includes a dielectric block, a laser light source for generating a light beam, an optical system for causing the light beam to enter the interface between the dielectric block and a metal film at various incident angles, and a light detection unit for detecting a parallelized light beam totally reflected at the interface. Properties are measured while causing a reference molecule, of substantially the same size and the same refractive index as an analysis object molecule, to adhere onto the metal film. The reference molecule is removed from the metal film, and the position of a dark line is measured while the measurement chip retains a sample. The position of a dark line of the analysis object molecule is detected by calibrating sensitivity based on the detection result of the position of the dark line while causing the reference molecule to adhere onto the metal film.

6 Claims, 7 Drawing Sheets

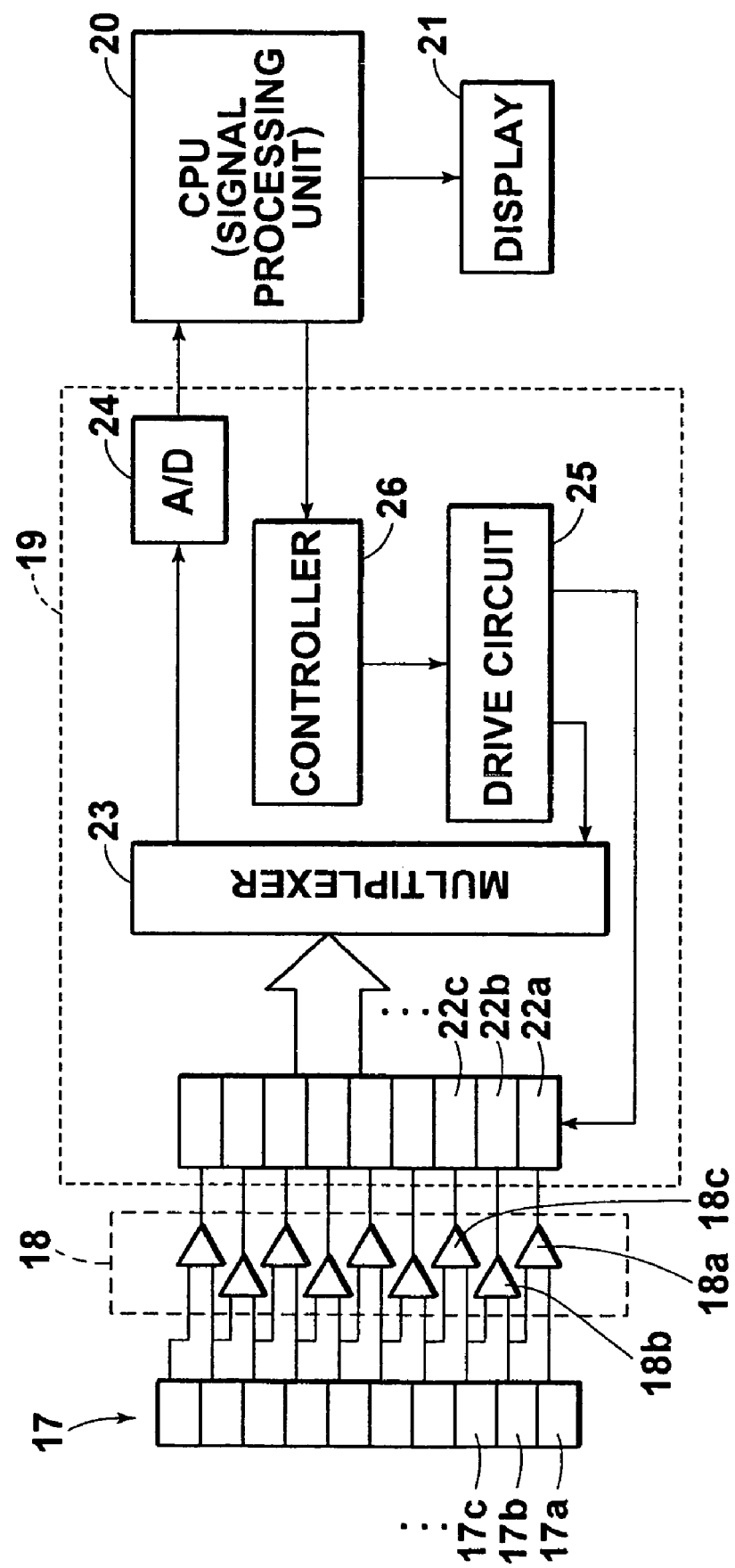

MEASUREMENT METHOD AND APPARATUS

BACKGROUND OF THE INVENTION

1. Field of the Invention

The present invention relates to a measurement method and a measurement apparatus utilizing attenuated total reflection. In the measurement method and apparatus, a light beam is totally reflected at an interface between a thin film layer, which is in contact with a sample, and a dielectric block to generate an evanescent wave. Then, a variation in the intensity of the totally reflected light beam is measured to analyze a sample.

2. Description of the Related Art

Free electrons in metal vibrate in a group, and a compression wave is generated. The compression wave is called a plasma wave. When the compression wave, which is generated on a surface of the metal, is quantized, it is called a surface plasmon.

Conventionally, various surface plasmon measurement apparatuses utilizing a phenomenon of the surface plasmon, excited by a light wave, have been proposed to analyze the properties of substances to be measured. Particularly, an apparatus using a system called the Kretschmann configuration is well-known among the surface plasmon measurement apparatuses (Japanese Unexamined Patent Publication No. 6(1994)-167443).

Basically, the surface plasmon measurement apparatus using the above-mentioned system includes a dielectric block, for example, in a prism shape, a metal film, which is formed on a surface of the dielectric block and brought into contact with a substance to be measured, such as sample liquid, a light source for generating a light beam, an optical system for causing the light beam to enter the dielectric block at various angles so that total reflection conditions are satisfied at the interface between the dielectric block and the metal film, and a light detection means for detecting a surface plasmon resonance state, namely an attenuated total reflection state, by measuring the intensity of the light beam, which is totally reflected at the interface.

A relatively thin light beam may be caused to enter the interface by changing the incident angle so that the light beam enters the interface at various incident angles as described above. Alternatively, a relatively thick light beam in a convergence light state or divergence light state may be caused to enter the interface so that the light beam includes components that enter the interface at various angles. In the former case, a reflection angle of the light beam changes according to the change in the incident angle of the light beam, which enters the interface, and the light beam may be detected by a small light detector, which moves synchronously with the change in the reflection angle. Alternatively, the light beam may be detected by an area sensor, which extends along the direction of the change in the reflection angle. In the latter case, the light beams may be detected by an area sensor, which extends in a direction so that each of the light beams reflected at various reflection angles may be detected.

In the surface plasmon measurement apparatus structured as described above, when the light beam is caused to enter the metal film at a specific incident angle, which is larger than or equal to a total reflection angle, an evanescent wave is generated. The electric field of the evanescent wave is distributed in the substance to be measured, which is in contact with the metal film. Then, surface plasmon is excited by the evanescent wave at the interface between the metal film and the substance to be measured. When a wave number vector of the evanescent wave is equal to the wave number of the surface plasmon, and the wave numbers are matched, the evanescent wave and the surface plasmon resonate. Then, light energy is transferred to the surface plasmon. Therefore, the intensity of the light, which was totally reflected at the interface between the dielectric block and the metal film, sharply decreases. Generally, the decrease in the intensity of the light is detected as a dark line by the light detection means. The resonance as described above occurs only if the incident beam is p polarized. Therefore, it is necessary to set in advance so that the light beam enters the interface in p polarization.

If the wave number of the surface plasmon is obtained based on an incident angle, at which attenuated total reflection (ATR) occurs, namely an attenuated total reflection angle θsp, the dielectric constant of the substance to be measured may be obtained. Specifically, if the wave number of the surface plasmon is Ksp, an angular frequency of the surface plasmon is ω, the speed of light in a vacuum is c, and the dielectric constants of the metal and the substance to be measured are $\epsilon_m$ and $\epsilon_s$, respectively, the following relationship is satisfied:

$$k_{sp}(\omega) = \frac{\omega}{c}\sqrt{\frac{\varepsilon_m(\omega)\varepsilon_s}{\varepsilon_m(\omega)+\varepsilon_s}}$$

Specifically, if the attenuated total reflection angle θsp is obtained, the dielectric constant $\epsilon_s$, namely, properties related to the refractive index of the substance to be measured, may be obtained. The attenuated total reflection angle θsp is an incident angle, at which the intensity of the reflection light decreases.

In the surface plasmon measurement apparatus as described above, an array-shaped light detection means as disclosed in U.S. Pat. No. 6,577,396 may be used to accurately measure the attenuated total reflection angle θsp in a wide dynamic range. In the light detection means, a plurality of light receiving elements is arranged in a predetermined direction. The plurality of light receiving elements is arranged in a direction so that each component of the light beam, which is totally reflected at various reflection angles at the interface, is received by a different light receiving element.

When the light receiving elements are arranged as described above, a differential means for differentiating a light detection signal, output from each of the light receiving elements of the array-shaped light detection means, with respect to the arrangement direction of the light receiving elements, is provided in many cases. Properties related to the refractive index of the substance to be measured is obtained based on a differential value, output by the differential means.

Further, a leaky mode measurement apparatus, described in "Spectrum Researches", Journal of The Spectroscopical Society of Japan, volume 47, No. 1, 1998, pp 21-23 and 26-27, is also known as a similar measurement apparatuses utilizing the attenuated total reflection (ATR). Basically, the leaky mode measurement apparatus includes a dielectric block, for example, in a prism shape, a clad layer formed on a face of the dielectric block, and an optical waveguide layer, which is formed on the clad layer and brought into contact with sample liquid. The leaky mode measurement apparatus also includes a light source for generating a light beam, an optical system for causing the light beam to enter the dielectric block at various angles so that total reflection conditions are satisfied at the interface between the dielectric block and the clad layer, and a light detection means for detecting an excitation state of a guided wave mode by measuring the intensity of the light beam, totally reflected at the interface. The excitation state is an attenuated total reflection state.

In the leaky mode measurement apparatus structured as described above, when the light beam is caused to enter the clad layer at an incident angle, larger than or equal to a total reflection angle, through the dielectric block, the light beam is transmitted through the clad layer. After the light beam is transmitted through the clad layer, only light with a specific wave number, which has entered at a specific incident angle, propagates in a guided wave mode in the optical waveguide layer. When the guided wave mode is excited as described above, a substantial part of the incident light is absorbed by the optical waveguide layer. Accordingly, the attenuated total reflection occurs, in which the intensity of light, totally reflected at the interface, sharply decreases. The wave number of the guided wave light depends on the refractive index of the substance to be measured on the optical waveguide layer. Therefore, if the specific incident angle, at which the attenuated total reflection occurs, is found, the refractive index of the substance to be measured and the properties of the substance to be measured, related to the refractive index, may be analyzed.

In the leaky mode measurement apparatus, the array-shaped light detection means, as described above, may be also used to detect the position of a dark line in a reflection light, generated by the attenuated total reflection. Further, the differential means as described above is also applied to the leaky mode measurement apparatus in many cases.

Further, the surface plasmon measurement apparatus and the leaky mode measurement apparatus, as described above, are used in random screening to find a specific substance, which will be combined with a desired sensing substance, in a research field such as drug discovery. In this case, a sensing substance, as the substance to be measured, is fixed on the thin film layer (the metal film in the case of the surface plasmon measurement apparatus, and the clad layer and the optical waveguide layer in the case of the leaky mode measurement apparatus). Sample liquid is added onto the sensing substance. In the sample liquid, various kinds of objects to be examined are dissolved in a solvent. Then, the attenuated total reflection angle θsp is measured at predetermined time intervals.

If the object to be examined in the sample liquid is an object that binds with the sensing substance, as time passes, the object to be examined binds with the sensing substance, and the refractive index of the sensing substance changes. Therefore, if the attenuated total reflection angle θsp is measured at predetermined time intervals to measure whether the attenuated total reflection angle θsp has changed, the binding state of the object to be measured and the sensing substance is measured. It is possible to judge whether the object to be measured is the specific substance, which binds with the sensing substance. As examples of the combination of the specific substance and the sensing substance, as described above, there are a combination of an antigen and an antibody and a combination of an antibody and an antibody. Specifically, a rabbit anti-human IgG (immunoglobulin G) antibody, as the sensing substance, may be fixed to the surface of the thin film layer, and a human IgG antibody may be used as the specific substance.

When measuring the binding state of the object to be measured and the sensing substance, it is not always necessary to detect the attenuated total reflection angle θsp itself. For example, the sample liquid is added to the sensing substance, and the variation in angle of the attenuated total reflection angle θsp after the addition may be measured. The binding state may be measured based on the magnitude of the variation in angle. If the array-shaped light detection means and the differential means, as described above, are applied to a measurement apparatus utilizing attenuated total reflection, the variation of a differential value reflects the variation in angle of the attenuated total reflection angle θsp. Therefore, the binding state of the sensing substance and the object to be measured may be measured based on the variation of the differential value.

In the measurement method and apparatus utilizing the attenuated total reflection as described above, sample liquid including a solvent and an object to be examined is supplied to a measurement chip by dropping. The measurement chip is cup-shaped or petri-dish-shaped, and a sensing substance is fixed on a thin film layer, formed on the bottom of the measurement chip in advance. Accordingly, the variation in angle of the attenuated total reflection angle θsp is measured.

When the sample liquid is supplied to the measurement chip, and the sensing substance and the object to be measured are bound with each other, the refractive index of the sensing substance changes. Accordingly, the attenuated total reflection angle θsp changes. Therefore, if after predetermined time has passed from the beginning of the measurement, the variation in angle of the attenuated total reflection angle θsp from the beginning of the measurement is obtained, it is possible to judge whether the object to be examined binds with the sensing substance. Further, if the object to be examined is bound with the sensing substance, it is possible to analyze the binding state of the object to be examined and the sensing substance, or the like. However, strictly speaking, the variation in angle of the attenuated total reflection angle θsp, detected by the measurement apparatus, does not accurately reflect the variation of the refractive index, caused by the combination of the sensing substance and the object to be examined. It is known that there is a difference in the measurement sensitivity depending on the thickness of the metal film in the measurement chip, the surface shape (coarseness) of the measurement chip, or the like.

Therefore, a sensitivity calibration method has been proposed to correct the difference in the sensitivity of each measurement chip. According to the method, every time that the measuring chip is changed, only solvent (buffer) is supplied to the measuring chip before measuring the properties of the sample liquid. The sensitivity of the measuring chip is detected based on a signal, which is output by measuring the properties of the solvent, and the sensitivity is calibrated.

Further, U.S. Patent Application Publication No. 20030075697 proposes a method for calibrating an actual measurement value based on a calibration curve. In this method, the properties of a plurality of kinds of reference samples of known refractive indices are measured, and the calibration curve is obtained based on the measurement result. U.S. Patent Application Publication No. 20030075697 discloses the use of liquid of a known refractive index as the reference sample and the use of a measurement chip (calibration tool), in which a solid material of a known refractive index (dielectric constant) is fixed (evaporated) on a thin film layer of the measurement chip.

However, the inventor of the present invention has found out that signal variation behaviors are different between a biomolecule, which is an object to be measured, and the buffer. Therefore, even if the sensitivity is calibrated by using the buffer, there is a difference in signals when the properties of an actual biomolecule are measured.

FIG. 7 is a graph illustrating a variation in the signal values of attenuated total reflection with respect to a physical property value k (an imaginary number, which is an absorption term, in a refractive index). Here, the signal is a SPR (surface plasmon resonance) signal, and its shift angle is the signal value. The physical property value k is proportional to the conductivity $\sigma$ of metal. In FIG. 7, the signal values of the buffer are represented by circles ($\bigcirc$), and the signal values of protein, which is a biomolecule, are represented by crosses (X). The signal values are standardized with respect to a reference physical property value, which is set to 1. As illustrated in FIG. 7, even if the physical property value k of metal changes by ±10%, there is substantially no difference in the signal values of the buffer. In contrast, there is a difference of approximately ±20% in the signal values of the protein, which is the biomolecule. Therefore, it is obvious that the sensitivity calibration method, using the buffer, according to the related art is not sufficient to detect the biomolecule.

Further, even if liquid having a known refractive index is used as a reference sample, as disclosed in U.S. Patent Application Publication No. 20030075697, when the properties of an actual biomolecule are measured, there seems to be a difference in signals in a similar manner to the case of correcting the sensitivity by using the buffer. Therefore, there is a problem that when a calibration tool is used, the sensitivity is not calibrated for each of the measurement chips.

SUMMARY OF THE INVENTION

In view of the foregoing circumstances, it is an object of the present invention to provide a measurement method and apparatus for reducing a measurement error due to individual difference in the measurement sensitivity of each measurement chip, thereby sufficiently improving the accuracy in measurement.

There is a problem that the sensitivity calibration by using the buffer or the reference sample, as described above, is not sufficient to calibrate the sensitivity. The inventor has reached the conclusion that the problem is caused by the properties of the evanescent wave, which is used in measurement, and the surface plasmon resonance, which is generated by the evanescent wave. The evanescent wave and the surface plasmon resonance are selectively sensitive only to a small sized substance such as a biomolecule in the vicinity of a gold film, but they are insensitive to a large size substance such as a buffer. Accordingly, the inventor has conceived the following invention.

A measurement method according to the present invention is a measurement method for analyzing an analysis object molecule by using a measurement apparatus utilizing attenuated total reflection, the apparatus including:

a light source for generating a light beam;

a measurement chip having a dielectric block transparent to the light beam, a thin film layer formed on a face of the dielectric block, and a sample retention mechanism for retaining a sample including the analysis object molecule on the surface of the thin film;

an incident light beam optical system for causing the light beam to enter the dielectric block at an incident angle so that total reflection conditions are satisfied at the interface between the dielectric block and the thin film layer; and a measurement means for measuring the position of a dark line in the light beam totally reflected at the interface, the method comprising the steps of:

measuring the position of the dark line while causing a reference molecule, of substantially the same size and substantially the same refractive index as the analysis object molecule, to adhere onto the thin film layer of the measurement chip;

removing the reference molecule from the thin film layer;

measuring the position of the dark line while causing the measurement chip to retain the sample; and calibrating the sensitivity of the measurement means, based on the measurement result of the position of the dark line while the reference molecule is adhered to the thin film, for each measurement chip.

The sensitivity calibration as described above may be performed either before or after measuring the position of the dark line while causing the measurement chip to retain the sample, as far as a measurement value after sensitivity calibration may be obtained as the result of the sensitivity calibration. However, it is preferable that the sensitivity calibration is performed before measuring the position of the dark line while causing the measurement chip to retain the sample.

A measurement apparatus according to the present invention is a measurement apparatus utilizing attenuated total reflection, comprising:

a light source for generating a light beam;

a measurement chip having a dielectric block transparent to the light beam, a thin film layer formed on a face of the dielectric block, and a sample retention mechanism for retaining a sample including an analysis object molecule on the surface of the thin film;

an incident light beam optical system for causing the light beam to enter the dielectric block at an incident angle so that total reflection occurs at the interface between the dielectric block and the thin film layer;

a measurement means for measuring the position of a dark line in the light beam totally reflected at the interface; and a sensitivity calibration means, which is provided on the thin film layer of the measurement chip in a detachable manner, for calibrating the sensitivity of the measurement means, based on the measurement result of the position of the dark line while the reference molecule, of substantially the same size and substantially the same refractive index as the analysis object molecule, is adhered to the thin film, for each measurement chip.

The term "measuring the position of a dark line" is synonymous with measuring an incident angle (total reflection angle) of a component, detected as the dark line, in the light beam. The position of the dark line may be measured by measuring the position of the dark line itself, or by measuring the variation of the position of the dark line from a predetermined position.

As the measurement apparatus as described above, there are the surface plasmon measurement apparatus, as described above, in which the metal film is used as the thin film layer, the leaky mode measurement apparatus, as described above, in which the clad layer formed on a face of the dielectric block and the optical waveguide layer, formed on the clad layer, are used as the thin film layer, and the like.

Further, a sensing medium may be provided on the thin film layer. In this case, an analysis object molecule and a reference object molecule may be fixed on the thin film layer through the sensing medium.

In the measurement method and measurement apparatus according to the present invention, the measurement result of the attenuated total reflection state, which is measured by using a plurality of kinds of reference sample liquid of a known refractive index is used as the reference measurement result. The measurement result obtained by measuring the properties of the sample is corrected based on the reference measurement result. Accordingly, a measurement error due to individual difference in the measurement sensitivity of the measurement apparatus may be reduced. Therefore, the accuracy in measurement may be improved.

BRIEF DESCRIPTION OF THE DRAWINGS

FIG. 3 is a block diagram illustrating the electric structure of the surface plasmon measurement apparatus;

DESCRIPTION OF THE PREFERRED EMBODIMENTS

Figure 1:
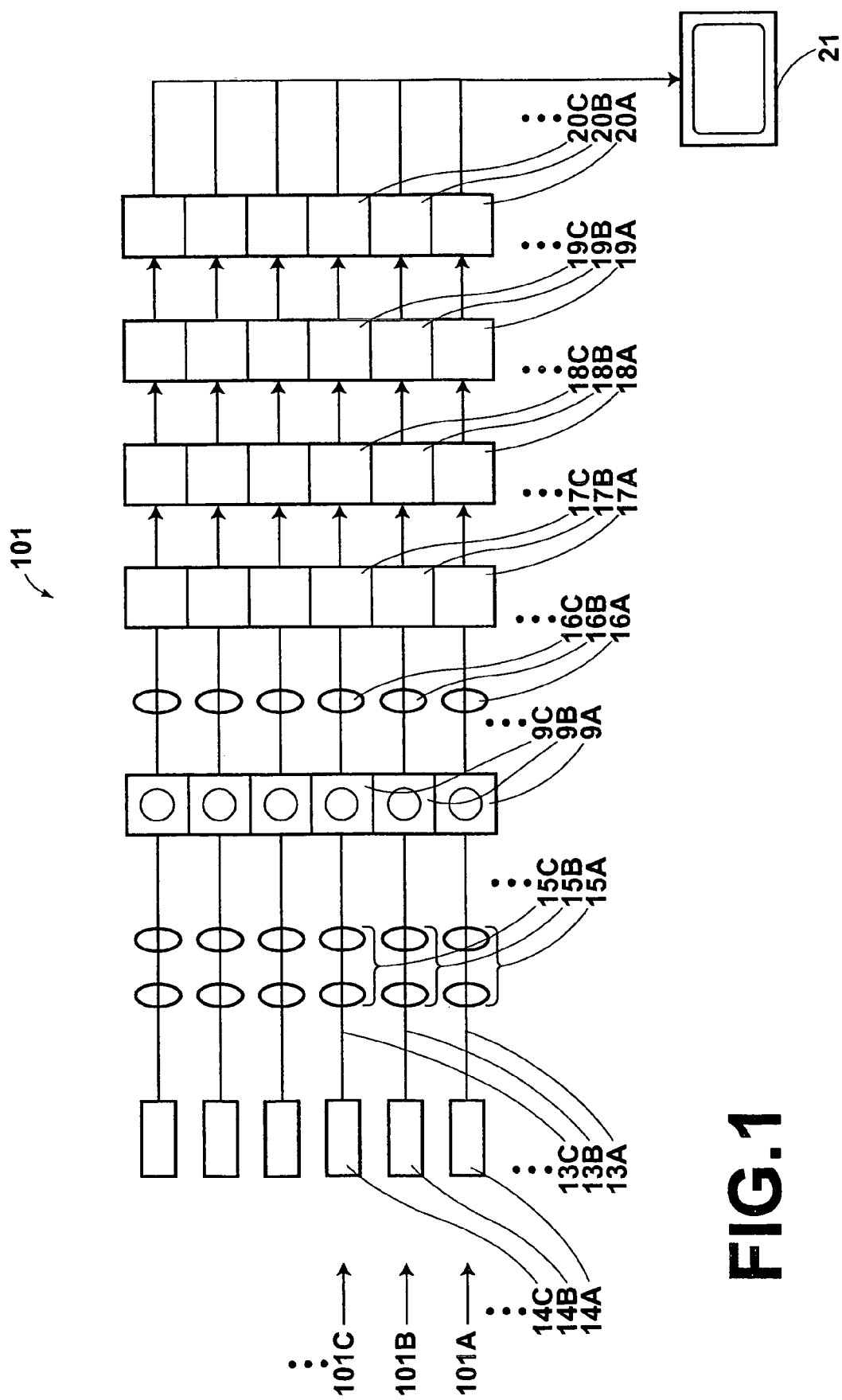
FIG. 1 is a plan view illustrating the schematic structure of a surface plasmon measurement apparatus according to an embodiment of the present invention.
Figure 2:
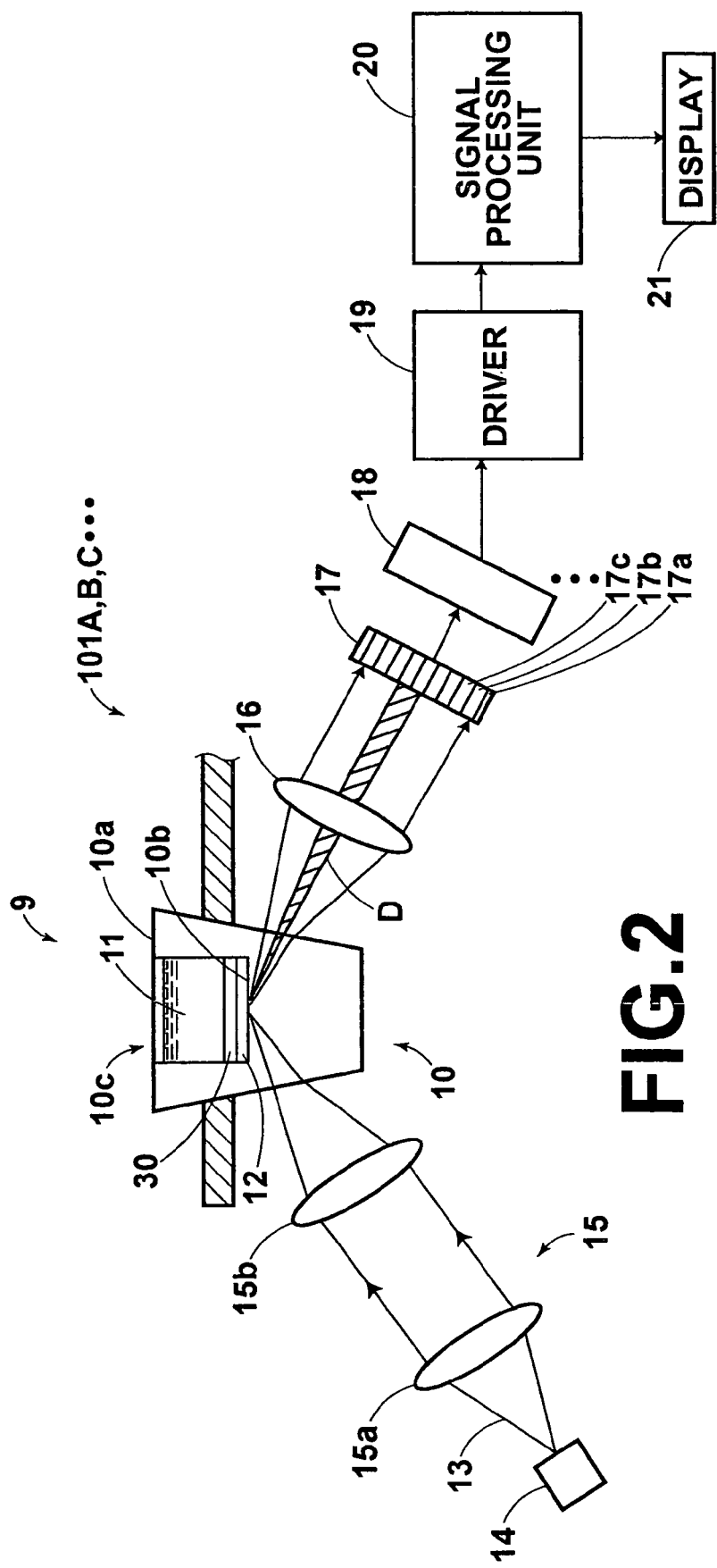
FIG. 2 is a diagram illustrating the side shape of the surface plasmon measurement apparatus.

Hereinafter, embodiments of the present invention will be described with reference drawings. A measurement apparatus according to an embodiment of the present invention is a surface plasmon measurement apparatus, which can simultaneously analyze a plurality of samples by causing light beams to enter a plurality of dielectric blocks in parallel. FIG. 1 is a plan view illustrating the schematic structure of the surface plasmon measurement apparatus in the present embodiment. FIG. 2 shows a side shape of the surface plasmon measurement apparatus.

The surface plasmon measurement apparatus includes a plurality of surface plasmon measurement units 101A, 101B, 101C, and the like, which are structured in a similar manner.

In the explanation of the structure of each of the measurement units, reference symbols A, B, C, and the like, which indicate individual elements, are omitted. Each of the measurement units includes a measurement chip 9, a laser light source 14, which is a light source for generating a light beam 13, an incident optical system 15 for causing the light beam 13 to enter the measurement chip 9, and a collimator lens 16, which parallelizes the light beam 13 reflected at the measurement chip 9 and emits the parallelized light beam to a light detector 17. Each of the measurement units also includes the light detector 17, which receives the light beam 13, emitted from the collimator lens 16, and detects the intensity of the light, and a differential amplifier array connected to the light detector 17. Each of the measurement units also includes a driver 19 connected to a differential amplifier array 18 and a signal processing unit 20. The signal processing unit 20 includes a computer system connected to the driver 19, or the like. The signal processing unit 20 also functions as a sensitivity calibration means for calibrating the sensitivity of each measurement chip 9. A measurement means for measuring the position of a dark line in the light beam includes the light detector 17, the differential amplifier array 18, the driver 19, and the signal processing unit 20.

The measurement chip 9 includes a dielectric block 10 and a metal film 12. The shape of the dielectric block 10 is a shape formed by cutting out an apex part of a quadrilateral pyramid from the quadrilateral pyramid. The apex is a point, at which four edges of the quadrilateral pyramid meet. Further, a concavity 10c, which functions as a sample retention mechanism for accumulating sample liquid 11, is formed on the bottom of the quadrilateral pyramid. The metal film 12 is formed on the bottom of the concavity 10c of the dielectric block 10. The metal film 12 is a thin film layer, made of gold, silver, copper, aluminum, or the like, for example. The dielectric block 10 may be formed by transparent resin or the like, for example. Further, a sensing medium 30, which will be described later, may be provided on the metal film 12. Here, a plurality of adjacent measurement chips 9 is connected to each other so that they can be handled in an integrated manner.

The incident optical system 15 includes a collimator lens 15a and a condenser lens 15b. The collimator lens 15a parallelizes the light beam 13, emitted from the laser light source 14. The condenser lens 15b causes the parallelized optical beam 13 to converge toward the interface 10b.

The light beam 13 is condensed by the condenser lens 15b as described above. Therefore, the light beam 13 includes components, which enter the interface 10b at various incident angles θ with respect to the interface 10b. The incident angles θ are larger than or equal to a total reflection angle. Therefore, the light beam 13, which is totally reflected at the interface 10b, includes components, which are totally reflected at various reflection angles. The incident optical system 15, as described above, may be structured so that the light beam 13 in a defocused state enters the interface 10b instead of condensing the light beam 13 to a point on the interface 10b. Accordingly, the light beam 13 is totally reflected in a wider area of the interface 10b. Therefore, the detection error in an attenuated total reflection state is averaged, and the accuracy in measurement of the attenuated total reflection angle can be improved.

The light beam 13 in a p polarized state should enter the interface 10b. Therefore, the laser light source 14 should be arranged so that the polarization direction of the light beam 13 becomes the predetermined direction as described above. Alternatively, the polarization direction of the light beam 13 may be controlled by using a wavelength plate so that the light beam 13 in the p polarized state enters the interface 10b.

The surface plasmon measurement apparatus 101 includes a single display means 21, which is connected to signal processing units 20A, 20B, 20C, and the like in the measuring units.

Analysis of sample by the surface plasmon measurement apparatus, structured as described above, will be described below.

As illustrated in FIG. 2, the light beam 13 emitted from the laser light source 14 converges on the interface 10b between the dielectric block 10 and the metal film 12 through the incident optical system 15.

The light beam 13, which converges on the interface 10b and which is totally reflected on the interface 10b, is detected by the light detector 17 through the collimator lens 16. The light detector 17 is a photodiode array, in which a plurality of photodiodes 17a, 17b, 17c, and the like are arranged in a row. The photodiodes are light receiving elements. The photodiodes are arranged so that the arrangement direction of the photodiodes is substantially in parallel with a paper face, illustrated in FIG. 2, and substantially vertical to a propagation direction of the light beam 13, which is parallelized through the collimator lens 16 and enters the light detector 17. Therefore, each of components of the light beam 13, which is totally reflected on the interface 10b at various reflection angles, is received by different photodiodes 17a, 17b, 17c, or the like. Then, the light detector 17 outputs a signal indicating the intensity distribution of the light beam 13, detected by each of the photodiodes 17a, 17b, 17c, and the like.

A component of the light beam 13, which has entered the interface 10b at a specific incident angle θsp, excites surface plasmon at the interface between the metal film 12 and a substance, which is in contact with the metal film 12. Therefore, the intensity of the reflection light of the light sharply decreases. Specifically, the specific incident angle θsp is an attenuated total reflection angle. When the incident angle is θsp, the intensity of the reflection light is the minimum. A region, in which the intensity of the reflection light decreases, is observed as a dark line in the light beam 13, which is totally reflected on the interface 10b. The dark line is represented as D in FIG. 2.

Next, processing of the signal indicating the intensity distribution of the light beam 13, which is output from the light detector 17, will be described in detail.

FIG. 3 is a block diagram illustrating the electric structure of the surface plasmon measurement apparatus. As illustrated in FIG. 3, the driver 19 includes sample-and-hold circuits 22a, 22b, 22c, or the like for sampling and holding an output from each of differential amplifiers 18a, 18b, 18c, and the like in the differential amplifier array 18. The driver 19 also includes a multiplexer 23, to which each output from the sample-and-hold circuits 22a, 22b, 22c, or the like is input. The driver 19 also includes an A/D converter 24 for digitizing an output from the multiplexer 23 to input to the signal processing unit 20. The driver 19 also includes a drive circuit 25 for driving the multiplexer 23 and the sample-and-hold circuits 22a, 22b, 22c, or the like, and a controller 26 for controlling the operation of the drive circuit 25 based on an instruction from the signal processing unit 20.

Each output from the photodiodes 17a, 17b, 17c, and the like is input to each of the differential amplifiers 18a, 18b, 18c, and the like in the differential amplifier array 18. In this case, outputs from two mutually adjacent photodiodes are input to the same differential amplifier. Therefore, an output from each of the differential amplifiers 18a, 18b, 18c, and the like may be regarded as a result obtained by differentiating light detection signals, output from the plurality of photodiodes 17a, 17b, 17c, and the like, with respect to the arrangement direction of the photodiodes.

An output from each of the differential amplifiers 18a, 18b, 18c, and the like is sampled and held by the sample-and-hold circuits 22a, 22b, 22c, or the like, respectively, at predetermined timing, and input to the multiplexer 23. The multiplexer 23 inputs the output from each of the differential amplifiers 18a, 18b, 18c, and the like, which was sampled and held, to the A/D converter 24 in a predetermined order. The A/D converter 24 digitizes the outputs to input to the signal processing unit 20.

Figure 4A:
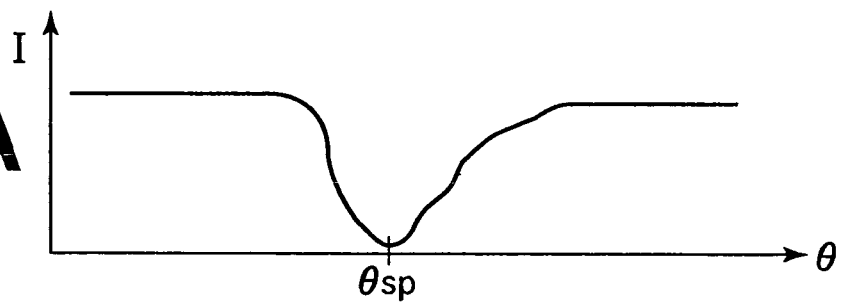
FIG. 4A is a diagram illustrating a relationship between an incident angle of a light beam at an interface and an output from a differential amplifier.

FIG. 4 is a diagram for explaining a relationship between the intensity of the light beam 13, which is totally reflected at the interface 10b, at each incident angle θ to the interface 10b, and an output from the differential amplifier 18a, 18b, 18c, or the like. Here, it is assumed that the relationship between the incident angle θ, at which the light beam 13 enters the interface 10b, and light intensity I of the light beam 13, which is reflected as described above, is as illustrated in a graph of FIG. 4A.

Figure 4B:
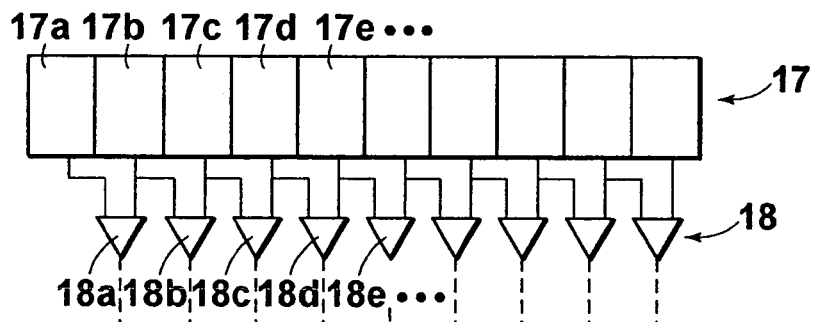
FIG. 4B is a diagram illustrating a relationship between an incident angle of a light beam at the interface and an output from the differential amplifier.

FIG. 4B illustrates the arrangement direction of the photodiodes 17a, 17b, 17c, and the like, which are placed in a row. As described above, there is one-to-one correspondence between the position of each of the photodiodes 17a, 17b, 17c, and the like with respect to their arrangement direction and the incident angle θ.

Figure 4C:
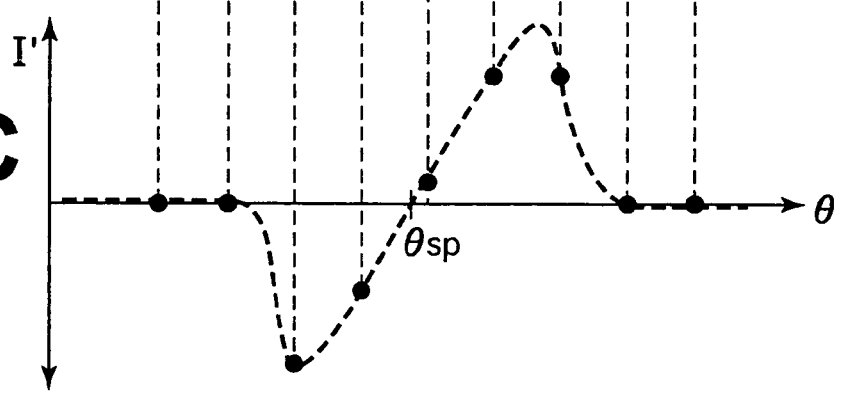
FIG. 4C is a diagram illustrating a relationship between an incident angle of a light beam at the interface and an output from the differential amplifier.

FIG. 4C illustrates a relationship between the position of each of the photodiodes 17a, 17b, 17c, and the like with respect to their arrangement direction, namely the incident angle θ, and an output I' (differential value of the intensity I of reflection light) from the differential amplifier 18a, 18b, 18c, or the like. Here, measurement of the position of the dark line is detection of the position of the dark line in the photodiode array. The detection of the position of the dark line may be regarded as detection of a corresponding incident angle θ.

The signal processing unit 20 selects, based on the value of the differential value I' input from the A/D converter 24, a differential amplifier (the differential amplifier 18e in the example of FIG. 4C), which outputs a positive differential value closest to the differential value I'=0 corresponding to the attenuated total reflection angle θsp, from the differential amplifiers 18a, 18b, 18c, and the like. The signal processing unit 20 also selects a differential amplifier (the differential amplifier 18d in the example of FIG. 4C), which outputs a negative differential value closest to the differential value I'=0 corresponding to the attenuated total reflection angle θsp, from the differential amplifiers 18a, 18b, 18c, and the like. The signal processing unit 20 calculates the attenuated total reflection angle θsp based on the differential values, output by the selected differential amplifiers. In some cases, there is a differential amplifier, which outputs the differential value I'=0. In such case, the signal processing unit 20 calculates the attenuated total reflection angle θsp based on an output from the differential amplifier. After this, a similar operation to the operation described above is repeated at predetermined time intervals to calculate the attenuated total reflection angle θsp. A variation in angle from the beginning of the measurement is calculated, and displayed on the display means 21.

As described above, when the dielectric constant, namely the reflective index, of a substance, which is in contact with the metal film 12 of the measurement chip, changes, the attenuated total reflection angle θsp changes accordingly. Therefore, if as time passes, the variation in angle of the attenuated total reflection angle θsp is continued to be measured, the variation in the refractive index of the substance, which is in contact with the metal film 12, may be examined.

Generally, a self-assembled monolayer (SAM) film, dextrin, or the like is provided on the metal film 12 so that an analysis object molecule is effectively adsorbed onto the metal film 12.

Further, when a sensing medium 30, which binds with a specific substance in the sample liquid 11, is fixed on the metal film 12, the refractive index of the substance on the metal film 12 changes depending on the binding state of the sample liquid 11 and the sensing medium 30. Therefore, if the differential value I' is continued to be measured, the variation in the binding state may be examined. As an example of the combination of the specific substance and the sensing medium 30, as described above, there is an antigen and an antibody, or the like.

Strictly speaking, the variation in angle of the attenuated total reflection angle θsp, measured at the measurement apparatus as described above, does not accurately reflect the variation in the refractive index of a substance, which is in contact with the metal film 12 of the measurement chip and/or which is in the vicinity of the metal film 12. In some cases, there is some error due to individual differences in the measurement sensitivity of the measurement chip.

Here, oligonucleotide (13-mer) of a known base sequence and molecular weight is used as the sensing medium 30. Sample liquid, including oligonucleotide, of which the base sequence or the like is not specified, is dispensed onto the measuring chips to detect a mismatch. Processing will be described with reference to FIGS. 5A through 5D. FIGS. 5A through 5D are schematic diagrams illustrating the state of the metal film 12 on the concavity 10c of the measurement chip 10 during the measurement procedure.

Figure 5A:
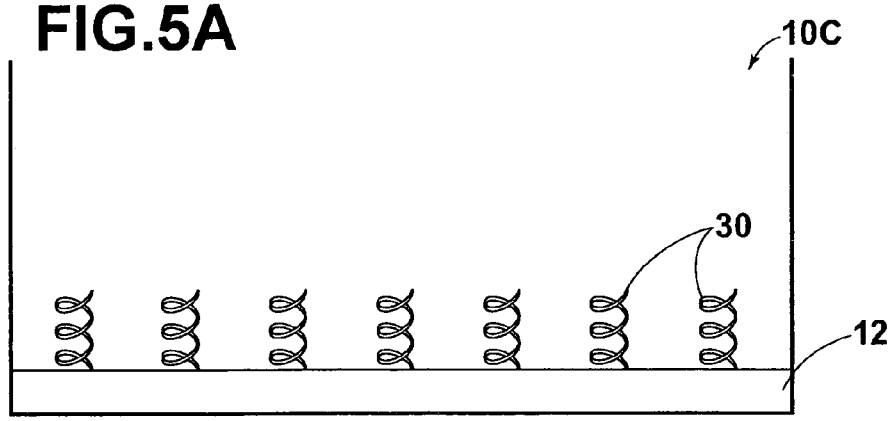
FIG. 5A is a schematic diagram for explaining a measurement method according to the present invention.
Figure 5B:
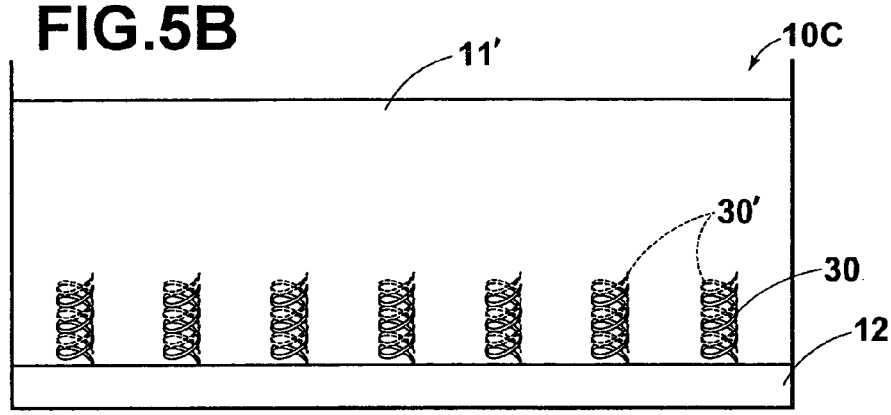
FIG. 5B is a schematic diagram for explaining the measurement method according to the present invention.

First, a gold film is used as the metal film 12. Oligonucleotide (13-mer) of a known base sequence and molecular weight is immobilized on the metal film 12 (FIG. 5A).

Then, the oligonucleotide 30 on the gold film 12 is bound with a complementary strand (13-mer) 30' as a reference molecule of a known base sequence and molecular weight, namely refractive index (SPR signal value), to detect a SPR signal. Specifically, reference liquid 11' including the complementary strand 30' is dispensed onto the measurement chip, and a SPR signal is detected after a predetermined time. Accordingly, a difference Δθ between a SPR signal value, obtained by using the complementary strand, and an original SPR signal value (known value) may be obtained. The sensitivity calibration means calibrates the sensitivity by using the difference Δθ as a sensitivity calibration value.

Figure 5C:
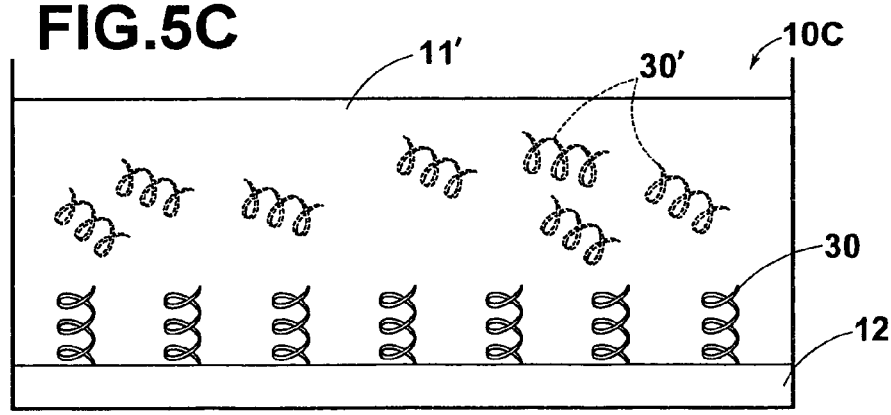
FIG. 5C is a schematic diagram for explaining the measurement method according to the present invention.

Then, the complementary strand is dissociated from the oligonucleotide on the gold film (FIG. 5C). The complementary strand may be dissociated from the oligonucleotide by increasing the temperature of the measurement chip to 90° C.

Figure 5D:
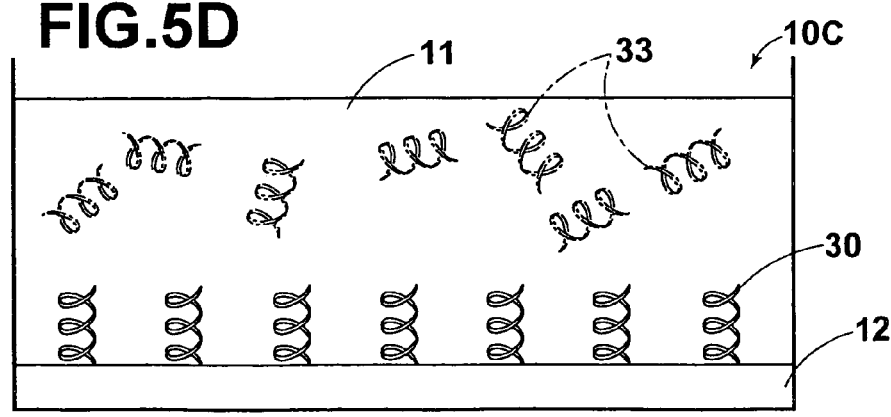
FIG. 5D is a schematic diagram for explaining the measurement method according to the present invention.

After the inside of the measurement chip is washed with a buffer, or the like, the sample liquid 11 including the oligonucleotide 33, of which the base sequence or like is not specified, is dispensed as the analysis object molecule (FIG. 5D). The SPR signal is detected continuously or when predetermined time has passed after the dispensation.

The signal processing unit 20 outputs a signal value after sensitivity calibration. The variation in sensitivity, due to the properties of the measurement chips 9, is corrected. Accordingly, it is possible to analyze whether the base sequence of the oligonucleotide, which is the analysis object, is identical with the base sequence of the oligonucleotide, which is the sensing medium. It is also possible to analyze the degree of identity, or the like.

The SPR signal value changes depending on the degree of identity of the base sequence of the oligonucleotide, which is the analysis object, with the base sequence of the oligonucleotide, which is the sensing medium 30. For example, the signal value (variation in the signal value) is slightly different depending on whether 10 bases are the same or all of 13 bases are same. In this case, if the sensitivity is not calibrated by using the difference Δθ, which was obtained before, the difference in the variation of the signal value between the oligonucleotide as the sensing medium 30 and the oligonucleotide as the analysis object might become unclear. However, if the sensitivity is calibrated as described above, the variation in the signal value may be detected at high accuracy. Therefore, more precise information may be obtained accurately.

In mismatch detection using the same oligonucleotide, properties were measured regarding 20 measurement chips without calibrating sensitivity by using the complementary strand, as described above. Properties were also measured regarding 20 measurement chips after calibrating sensitivity by using the complementary strand, as described above. According to the measurement result, when the sensitivity was not calibrated, the difference in the signals (CV value) among the 20 measurement chips was 9%. When the sensitivity was calibrated, the difference in the signals among the 20 measurement chips was 3%.

Next, a measurement method for measuring whether a predetermined protein is included in sample liquid will be described.

First, a gold film is used as the metal film. An immobilization film (carboxymethyldextran) is fixed on the gold film. The immobilization film includes abundant carboxy groups at its surface. The carboxymethyldextran functions as a medium for adsorbing the protein onto the gold film.

N-avidin (isoelectric point is approximately pH7), of a known molecular size and refractive index, is immobilized on the carboxymethyldextran by using an acetic acid buffer solution (approximately pH6). The surface of the carboxymethyldextran is negatively charged, and the N-avidin is positively charged. Therefore, the N-avidin is effectively immobilized on the carboxymethyldextran by electrostatic action. Here, the size and refractive index of the N-avidin is substantially the same as that of the protein, which is the analysis object.

A SPR signal is detected while the N-avidin is immobilized. The sensitivity calibration means calibrates the sensitivity by using the difference Δθ from the original signal value, which is obtained based on the refractive index of the N-avidin, as the sensitivity calibration amount.

Then, the N-avidin is dissociated from the carboxymethyldextran by changing the pH of the buffer to approximately pH9. When the pH is changed to approximately 9, both the surface of the carboxymethyldextran and the N-avidin are negatively charged. Therefore, the N-avidin can be dissociated by electrostatic repulsion. However, empirically, if only the pH of the buffer is changed, the immobilized N-avidin is not completely desorbed. Therefore, after the N-avidin is desorbed by using the buffer of approximately pH9, the N-avidin is further washed with a NaOH solution of 2M (molarity). Accordingly, the immobilized N-avidin can be completely removed.

After then, sample liquid including a protein as an analysis object molecule is dispensed. When a SPR signal is measured continuously or after predetermined time has passed, it is possible to detect whether the protein is a predetermined protein.

Figure 6:
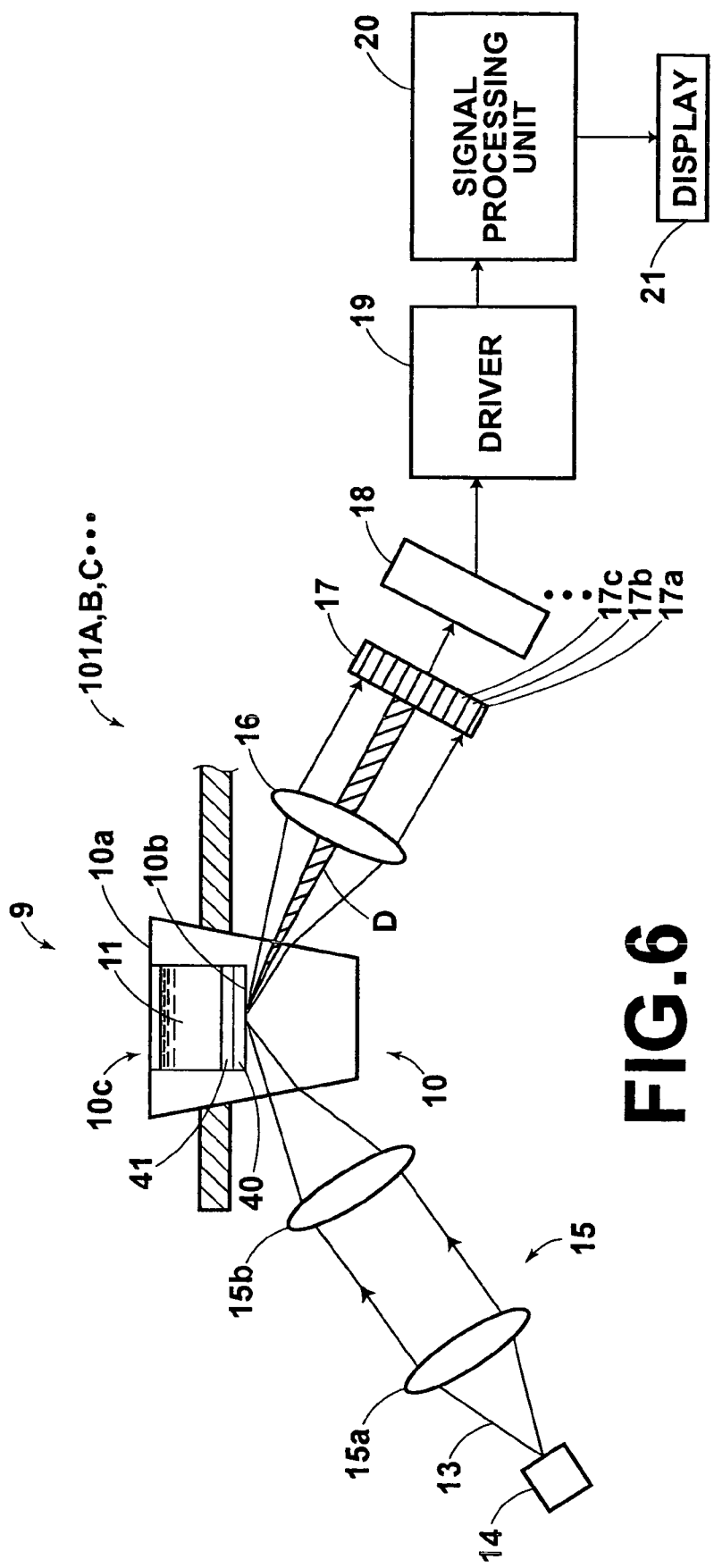
FIG. 6 is a diagram illustrating an example of a leaky mode measurement apparatus.
Figure 7:
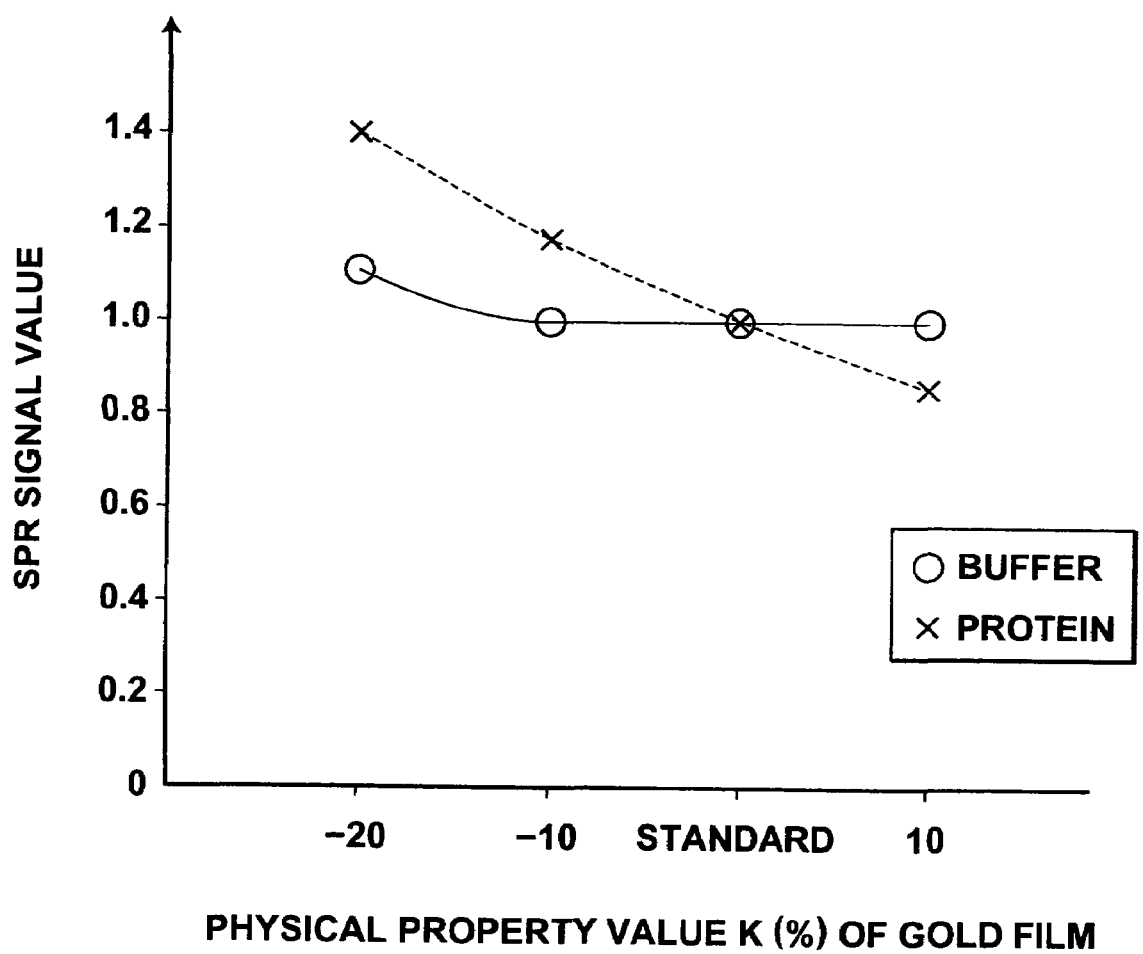
FIG. 7 is a graph illustrating a variation in SPR signals due to a variation in the physical property values of metal.

The surface plasmon measurement apparatus as described above may be provided as a leaky mode measurement apparatus by changing a part of the structure. FIG. 6 shows a side view of the leaky mode measurement apparatus. A part of the surface plasmon measurement apparatus 101, as described above, is modified in the leaky mode measurement apparatus. In FIG. 6 the same reference numerals are assigned to the elements similar to those in FIG. 2. Detailed descriptions on the similar elements are omitted unless particularly required.

The leaky mode measurement apparatus is structured so that the measurement chip 9 is used in a similar manner to the surface plasmon measurement apparatus as described above. A concavity 10c is formed on the upper surface of the measurement chip 9, and a clad layer 40 is formed on the bottom of the concavity 10c. An optical waveguide layer 41 is formed on the clad layer. The clad layer 40 and the optical waveguide layer 41 together form a thin film layer.

The dielectric block 10 is formed by using a synthetic resin, or optical glass such as BK7, for example. Meanwhile, the clad layer 40 is formed in a thin-film shape by using a dielectric of lower refractive index than that of the dielectric block 10, or a metal such as gold. The optical waveguide layer 41 is also formed in a thin-film shape by using a dielectric of lower refractive index than that of the clad layer 40, such as PMMA (polymethylmethacrylate), for example. The thickness of the clad layer 40 is 36.5 nm when the clad layer 40 is formed by using a thin gold film, for example. The thickness of the optical waveguide layer 41 is approximately 700 nm when the optical waveguide layer 41 is formed by using the PMMA, for example.

In the leaky mode measurement apparatus, structured as described above, when the light beam 13, emitted from the laser light source 14, enters the clad layer 40, at an incident angle, which is larger than or equal to a total reflection angle, through the dielectric block 10, a substantial part of the components of the light beam 13 are totally reflected at the interface 10b between the dielectric block 10 and the clad layer 40. However, light of a specific frequency, which has been transmitted through the clad layer 40, and which has entered the optical waveguide layer 41 at a specific incident angle, propagates in the optical waveguide layer 41 in a guided wave mode. When the guided wave mode is excited, as described above, a substantial part of the incident light, which has entered at the specific incident angle, is absorbed by the optical waveguide layer 41. Therefore, attenuated total reflection occurs, in which the intensity of light, which has entered the interface 10b at the specific angle, and is totally reflected, sharply decreases.

The wave number of the guided wave light in the optical waveguide layer 41 depends on the refractive index of the sample liquid 11 on the optical waveguide layer 41. Therefore, if an attenuated total reflection angle, which is the specific incident angle, at which the attenuated total reflection occurs, is found, the refractive index of the sample liquid 11 and related properties of the sample liquid 11 may be analyzed.

In the leaky mode measurement apparatus as described above, a sensitivity calibration means similar to that of the surface plasmon measurement apparatus, as described above, may be provided to realize a similar effect.

What is claimed is:

1. A measurement method for analyzing an analysis object molecule by using a measurement apparatus utilizing attenuated total reflection, the apparatus including:

a light source for generating a light beam;

a measurement chip having a dielectric block transparent to the light beam, a thin film layer formed on a face of the dielectric block, and a sample retention mechanism for retaining a sample including the analysis object molecule on the surface of the thin film;

an incident light beam optical system for causing the light beam to enter the dielectric block at an incident angle so that total reflection conditions are satisfied at the interface between the dielectric block and the thin film layer; and a measurement means for measuring the position of a dark line in the light beam totally reflected at the interface, the method comprising the steps of:

measuring the position of the dark line while causing a reference molecule, of substantially the same size and substantially the same refractive index as the analysis object molecule, to adhere onto the thin film layer of the measurement chip;

removing the reference molecule from the thin film layer; measuring the position of the dark line while causing the measurement chip to retain the sample; and calibrating the sensitivity of the measurement means, based on the measurement result of the position of the dark line while the reference molecule is adhered to the thin film, for each measurement chip.

2. A measurement method as defined in claim 1, wherein the calibration of the sensitivity is performed before the position of the dark line is measured while causing the measurement chip to retain the sample.

3. A measurement apparatus utilizing attenuated total reflection, comprising:

a light source for generating a light beam;

a measurement chip having a dielectric block transparent to the light beam, a thin film layer formed on a face of the dielectric block, and a sample retention mechanism for retaining a sample including an analysis object molecule on the surface of the thin film;

an incident light beam optical system for causing the light beam to enter the dielectric block at an incident angle so that total reflection occurs at the interface between the dielectric block and the thin film layer;

a measurement means for measuring the position of a dark line in the light beam totally reflected at the interface; and a sensitivity calibration means, which is provided on the thin film layer of the measurement chip in a detachable manner, for calibrating the sensitivity of the measurement means, based on the measurement result of the position of the dark line while the reference molecule, of substantially the same size and substantially the same refractive index as the analysis object molecule, is adhered to the thin film, for each measurement chip.

4. A measurement apparatus as defined in claim 3, wherein the measurement apparatus utilizing the attenuated total reflection is a surface plasmon measurement apparatus.

5. A measurement apparatus as defined in claim 4, wherein the thin film layer is made of one of gold, silver, copper, and aluminum.

6. A measurement apparatus as defined in claim 3, wherein the measurement apparatus utilizing the attenuated total reflection is a leaky mode measurement apparatus.

* * * * *